US00PP29230P3

(12) United States Plant Patent
Klemm et al.

(10) Patent No.: US PP29,230 P3
(45) Date of Patent: Apr. 10, 2018

(54) ***OSTEOSPERMUM* PLANT NAMED 'KLEOE15267'**

(50) Latin Name: ***Osteospermum ecklonis* Norl**
Varietal Denomination: KLEOE15267

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/530,207

(22) Filed: Dec. 12, 2016

(65) Prior Publication Data

US 2017/0290241 P1 Oct. 5, 2017

(30) Foreign Application Priority Data

Mar. 30, 2016 (QZ) ..... PBR 2016/0848

(51) Int. Cl.
*A01H 5/02* (2018.01)

(52) U.S. Cl.
USPC ..... Plt./360
CPC ..... *A01H 5/025* (2013.01)

(58) Field of Classification Search
USPC ..... Plt./360
CPC ..... A01H 5/025
See application file for complete search history.

(56) References Cited

PUBLICATIONS http://www.balllandscape.com/pdf/Selecta-2016Catalog-15117.pdf; 2015; 126 pages.*

* cited by examiner

*Primary Examiner* — Kent L Bell
(74) *Attorney, Agent, or Firm* — James M. Weatherly; Bethany R. Roahrig; Cochran Freund & Young LLC

(57) ABSTRACT

A new *Osteospermum* plant particularly distinguished by having yellow inflorescences and a short to medium height.

1 Drawing Sheet

Genus and species: *Osteospermum ecklonis* Norl.
Variety denomination: 'KLEOE15267'.

CROSS REFERENCES TO RELATED APPLICATION

The current application claims the benefit of priority to Community Plant Variety Rights application number 2016/0848, as filed on Mar. 30, 2016, the entire contents of which are incorporated herein by reference.

BACKGROUND OF THE NEW PLANT

The present invention comprises a new and distinct variety of *Osteospermum*, botanically known as *Osteospermum ecklonis* Norl, and hereinafter referred to by the variety name 'KLEOE15267'. 'KLEOE15267' originated from a cross-pollination between the proprietary female *Osteospermum* variety 'OE-2006-0149' (unpatented), and the proprietary male *Osteospermum* variety 'Balvoyelo' (U.S. Plant Pat. No. 21,122).

In the summer of 2011, the two *Osteospermum* parental lines 'OE-2006-0149' and 'Balvoyelo' were crossed in Nairobi, Kenya, and seeds were obtained. The seeds were sown and plants were grown for evaluation. A plant line was selected in spring 2012 and named 'KLEOE15267'. In spring 2012, 'KLEOE15267' was first vegetatively propagated by terminal cuttings in Nairobi, Kenya.

'KLEOE15267' was found to reproduce true to type in successive generations of asexual propagation via terminal cuttings.

SUMMARY

The following are the most outstanding and distinguishing characteristics of this new variety when grown under normal horticultural practices in Stuttgart, Germany.

1. Yellow inflorescence color; and
2. Short to medium height.

DESCRIPTION OF THE PHOTOGRAPH

This new *Osteospermum* plant is illustrated by the accompanying photograph, which shows the plant with inflorescences grown in a pot. The photograph is of a two-month-old plant grown in a controlled greenhouse environment in Stuttgart, Germany in July 2016. The colors shown are as true as can be reasonably obtained by conventional photographic procedures.

DESCRIPTION OF THE NEW VARIETY

The following detailed descriptions set forth the distinctive characteristics of 'KLEOE15267'. The data which define these characteristics were collected from asexual reproductions carried out in Stuttgart, Germany. Data was collected on two-month-old plants grown in a controlled greenhouse environment in Stuttgart, Germany under greenhouse conditions in July 2016, with a sticking in May 2016 and potting in June 2016. Color references are to The R.H.S. Colour Chart of The Royal Horticultural Society of London (R.H.S.), 5th edition (2007).

Classification:

*Family*.—Compositae.

*Botanical*.—*Osteospermum ecklonis* Norl.

*Common*.—*Osteospermum*, African Daisy.

*Designation*.—'KLEOE15267'.

Parentage:

*Female parent*.—*Osteospermum* line 'OE-2006-0149' (unpatented).

*Male parent*.—*Osteospermum* line 'Balvoyelo' (U.S. Plant Pat. No. 21,122).

Plant:

*Form and habit*.—Herbaceous perennial, but usually cultivated as an annual; not frost resistant.

*Growth habit*.—Semi-upright.

*Branching habit*.—Freely branching.

*Height* (*from top of soil, including inflorescence*).—About 28.0 cm.

*Width* (*including inflorescences*).—About 15.0 cm.

*Propagation*.—Terminal cuttings.

*Time to produce a finished flowering plant*.—About 7 weeks.

*Time to initiate and develop roots*.—Between 3 and 4 weeks.

*Root description*.—Freely rooting, light tan in color.

Leaves:

*Arrangement*.—Alternate.

*Shape*.—Obovate.

*Apex*.—Acute.

*Base*.—Acute.

*Margin*.—Medium serrate.

*Immature color*.—Upper surface: RHS 137A. Lower surface: RHS 137C.

*Mature color*.—Upper surface: RHS N137D. Lower surface: RHS 137B.

*Length*.—Up to 8.0 cm.

*Width*.—Up to 4.0 cm.

*Texture*.—Upper and lower surfaces: Leathery smooth, covered with fine hairs.

*Petioles*.—Absent.

*Venation pattern*.—Pinnate.

*Venation color*.—Upper surface: RHS 137C. Lower surface: RHS 137B.

Stems:

*Total number of branches per plant* (*calculated at the base of the plant*).—Around 5.

*Length*.—Up to 17.0 cm.

*Diameter*.—0.4 cm.

*Internode length*.—1.0 cm to 2.0 cm.

*Color*.—RHS 144B.

*Texture*.—With fine hairs.

*Anthocyanin*.—Absent.

Buds:

*Shape*.—Obovate.

*Length*.—About 0.7 cm.

*Diameter*.—About 0.7 cm.

*Color* (*at tight bud just before the ray florets unfold*).—RHS 145C to RHS N144C.

Inflorescence:

*Type*.—Daisy, single.

*Blooming habit*.—Spring to autumn in Europe.

*Quantity of inflorescences per plant*.—Between 15 and 20.

*Lastingness of the inflorescences on the plant*.—About 2 weeks.

*Fragrance*.—Absent.

*Inflorescence diameter*.—About 6.0 cm.

*Inflorescence depth*.—About 1.0 cm.

*Disc diameter*.—About 1.0 cm.

Disc floret:

*Quantity per inflorescence*.—About 80.

*Shape*.—Oblanceolate.

*Tube color*.—Closed: RHS 153B. Mature: RHS 3B.

*Length*.—0.6 cm.

*Diameter* (*at apex*).—0.1 cm.

*Apex*.—Acute.

*Apex color*.—RHS 7A.

*Base*.—Acute.

*Base color*.—RHS 155C.

*Margin*.—Entire.

Ray floret:

*Quantity per inflorescence*.—About 16.

*Shape*.—Oblanceolate.

*Color*.—Upper surface: RHS 9A. Lower surface: RHS 11A and shade of RHS 59C with RHS 177A strips.

*Length*.—Around 3.3 cm.

*Width*.—Around 0.6 cm.

*Apex*.—Obtuse.

*Base*.—Acute.

*Margin*.—Entire.

*Texture*.—Upper surface: Smooth. Lower surface: Smooth and shiny.

*Peduncle*.—Length: Between 4.0 cm and 10.0 cm. Diameter: 0.2 cm. Texture: Rough with fine hairs. Color: RHS 144A.

Phyllaries:

*Texture*.—With fine hairs.

*Arrangement*.—Single.

*Observed quantity per plant*.—About 14.

*Shape*.—Lanceolate.

*Color*.—Upper surface: RHS 144A. Lower surface: RHS 144B.

*Length*.—About 1.0 cm.

*Width*.—About 0.2 cm.

*Apex*.—Narrowly acute.

*Base*.—Acute.

*Margin*.—Entire.

*Texture*.—Upper surface: With fine hairs. Lower surface: Shiny.

Reproductive organs:

*Androecium*.—Location: On the disc floret. Stamens: Quantity: 100 to 120. Shape: Filamentous. Filament length: 0.4 cm. Filament diameter: About 0.07 cm. Anther: Shape: Lanceolate. Color: RHS N92A. Length: 0.2 cm. Diameter: Less than 0.05 cm. Pollen: Color: RHS 14A. Amount: Moderate.

*Gynoecium*.—Location: On the base of the petals (ray floret) and reduced on disc florets. Pistils: Number: One per petal (ray floret). Length: 0.4 cm. Diameter: Less than 0.05 cm. Stigma: Color: RHS 59A. Shape: Split in two parts at the end. Length: 0.2 cm. Diameter: Less than 0.05 cm. Style: Color: RHS 70C. Length: 0.2 cm. Diameter: Less than 0.05 cm.

Fruit and seed set: None observed.

Disease and pest/insect resistance: No particular disease or insect resistance observed.

COMPARISON WITH PARENTAL LINES AND KNOWN VARIETY

'KLEOE15267' is a distinct variety of *Osteospermum* having a yellow inflorescence color and short to medium height. 'KLEOE15267' is distinguished from its parents as described in Table 1:

TABLE 1

Comparison with Parental Lines

| Trait | 'KLEOE15267' | Female parent 'OE-2006-0149' | Male Parent 'Balvoyelo' |
|---|---|---|---|
| Inflorescence color | Yellow | Orange yellow | Yellow |
| Plant height | Short to medium | Medium | Medium to tall |

'KLEOE15267' is a distinct variety of *Osteospermum* having a yellow inflorescence color and short to medium height. 'KLEOE15267' is most similar to the *Osteospermum* plant named 'KLEOE14243' (U.S. Plant Pat. No. 27,344). Differences between the two varieties are described in Table 2:

TABLE 2

Comparison with Similar Variety

| Trait | Variety 'KLEOE15267' | Commercial line 'KLEOE14243' |
|---|---|---|
| Plant height | Short to medium | Medium |

We claim:

1. A new and distinct variety of *Osteospermum* plant named 'KLEOE15267' as shown and described herein.

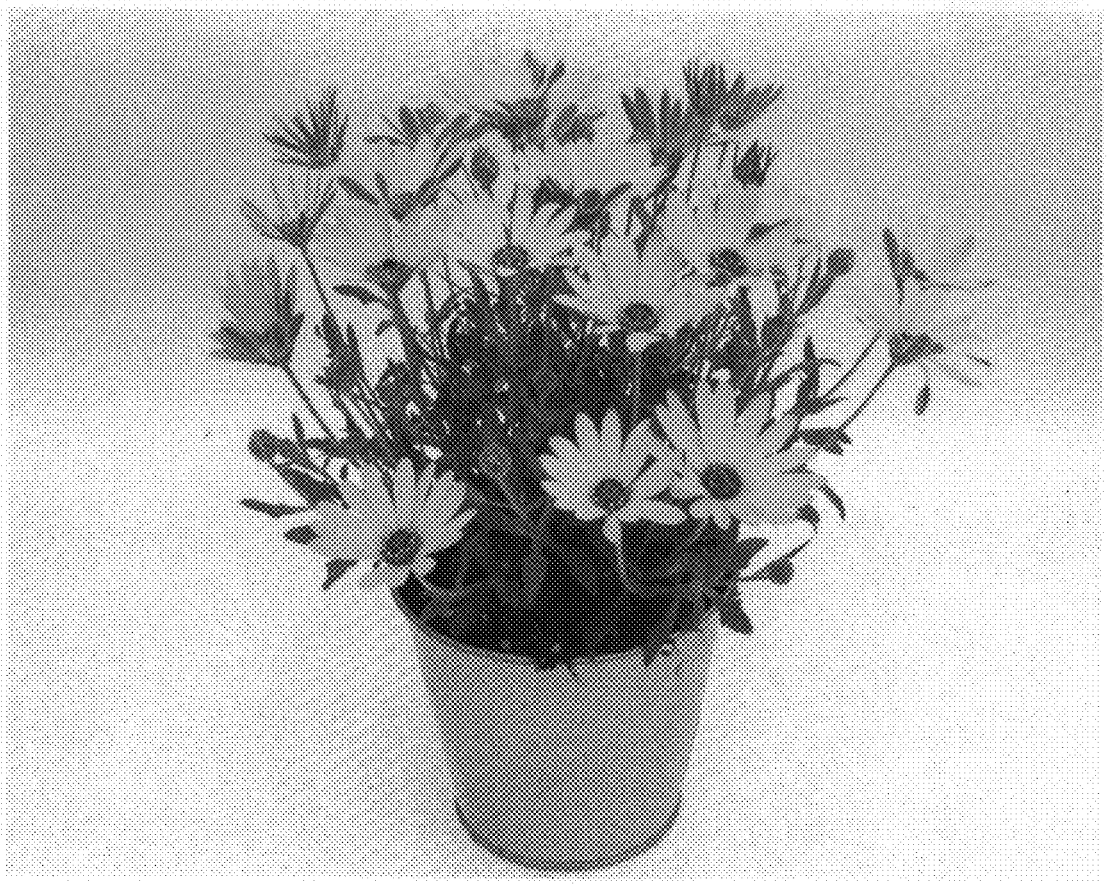

* * * * *